(12) United States Patent
Chang

(10) Patent No.: US 8,420,624 B2
(45) Date of Patent: *Apr. 16, 2013

(54) METHODS FOR TREATING OR PREVENTING SYMPTOMS OF HORMONAL VARIATIONS

(75) Inventor: Yeong-Ming Chang, Taichung (TW)

(73) Assignee: Yung Shin Pharm. Ind. Co., Ltd., Taichung (TW)

( * ) Notice: Subject to any disclaimer, the term of this patent is extended or adjusted under 35 U.S.C. 154(b) by 553 days.

This patent is subject to a terminal disclaimer.

(21) Appl. No.: 12/326,773

(22) Filed: Dec. 2, 2008

(65) Prior Publication Data
US 2009/0143344 A1    Jun. 4, 2009

Related U.S. Application Data

(60) Provisional application No. 60/992,265, filed on Dec. 4, 2007.

(51) Int. Cl.
*A01N 45/00* (2006.01)
*A61K 31/56* (2006.01)

(52) U.S. Cl.
USPC .................. 514/169; 514/171; 514/177

(58) Field of Classification Search .......... 514/169, 514/171, 177
See application file for complete search history.

(56) References Cited

U.S. PATENT DOCUMENTS

| 4,096,254 A | 6/1978 | Benson et al. |
| 4,499,019 A | 2/1985 | Thominet et al. |
| 5,654,011 A | 8/1997 | Jackson et al. |
| 6,297,243 B1 | 10/2001 | Groendahl |
| 6,310,098 B1 | 10/2001 | Guttuso, Jr. |
| 6,358,944 B1 | 3/2002 | Lederman et al. |
| 6,613,792 B1 | 9/2003 | Ellenberger et al. |
| 7,645,750 B2 | 1/2010 | Wu |
| 2004/0127489 A1 | 7/2004 | Pickar et al. |
| 2005/0118242 A1 | 6/2005 | Dudley et al. |
| 2005/0119248 A1 | 6/2005 | Buntinx |
| 2005/0256112 A1 | 11/2005 | Brodney et al. |
| 2006/0122127 A1 | 6/2006 | Rao et al. |
| 2007/0264358 A1 | 11/2007 | Wittlin |

FOREIGN PATENT DOCUMENTS

| WO | WO 2004/004784 A1 | | 1/2004 |
| WO | WO 2006/051111 | * | 5/2006 |
| WO | WO 2006/051111 A1 | | 5/2006 |

OTHER PUBLICATIONS

Stearns (Current Oncology Reports (2004) 6:285-290).*
Leysen et. al. (International Journal of Psychiatry in Clinical Practice (1998) 2:S3-S17).*
Casper et al., "Objective measurement of hot flushes associated with the premenstrual syndrome", Fertility Sterility, 2: 341-344, 1987.
Chen, Yaqiong et al., "Changes of plasma serotonin precursor metabolite concentrations in postmenopausal women with hot flushes," Chin J. Obstet Gynecol, Dec. 2002, 37(12), p. 726-728.
Connolly, Moira, "Premenstrual syndrome: an update on definitions, diagnosis and management", Advances Psychiatric Treatment, 7: 469-477, 2001.
Grady, Deborah, "Management of Menopausal Symptoms", N. Engl. J. Med. 355: 2338-47, 2006.
Hahn et al., "Menopausal-like hot flashes reported in women of reproductive age", Fertility Sterility, 70: 913-918, 1998.
Sipe, Kimberly et al., "Serotonin 2A receptors modulate tail-skin temperature in two rodent models of estrogen deficiency-related thermoregulatory dysfunction," Brain Research, vol. 1028 (2004) pp. 191-202.
Suvanto-Luukonen et al., "Citalopram and fluoxetine in the treatment of postmenopausal symptoms: a prospective, randomized, 9-month, placebo-controlled, double-blind study", Menopause, vol. 12, No. 1. pp. 18-26, 2005 (see Abstract).
Yonkers et al., "Premenstrual syndrome", Lancet, 371: 1200-1210, 2008.
Zylicz, Z. et al., "Flushing and Sweating in an Advanced Breast Cancer Patient Relieved by Olanzapine", Journal of Pain and Symptom Management, vol. 25, No. 6, Jun. 1, 2003, pp. 494-495.
Product Insert of Zyprexa by Lilly (Mar. 2009).
Product Insert of Clozaril by Novatis (Nov. 2004).

* cited by examiner

*Primary Examiner* — Marcos Sznaidman
(74) *Attorney, Agent, or Firm* — Perkins Coie LLP.; Viola T. Kung

(57) ABSTRACT

The present invention relates to methods for treating or preventing symptoms of hormonal variation. The method comprises the steps of administering an effective amount of a receptor antagonist to a subject having one or more symptoms of hormonal variations, wherein the receptor antagonist binds to at least one receptor selected from the group consisting of a serotonin type 2A ($5\text{-}HT_{2A}$) and a dopamine type 2 ($D_2$) receptors.

14 Claims, No Drawings

METHODS FOR TREATING OR PREVENTING SYMPTOMS OF HORMONAL VARIATIONS

This application claims the benefit of U.S. Provisional Application No. 60/992,265, filed Dec. 4, 2007, which is incorporated herein by reference in its entirety.

FIELD OF THE INVENTION

The present invention relates generally to treatment or prevention of symptoms of hormonal variation associated with menopause, surgery and/or androgen deprivation therapy, such as hot flashes, night sweats, and insomnia.

BACKGROUND

Hot flashes (also called vasomotor flashes) are the most common symptoms experienced by women who are perimenopausal or postmenopausal. Hot flashes are also a common and potentially chronic problem in men with prostate cancer who undergo androgen deprivation therapy (ADT). This is a major quality of life issue for a significant proportion of men receiving ADT. One report shows that the natural history of hot flashes in men, including variation in severity and frequency, has not been widely studied. Almost 70 percent of men who undergo surgical orchiectomy report hot flushes. About 70 to 80 percent of men on long-term androgen suppression have hot flushes, and 30 to 40 percent of these patients report that symptoms are a major source of discomfort (Steams, V., Ullmer, L., Lopez, J. F., Smith, Y., Isaacs, C., and Hayes, D. (2002) Hot flushes. Lancet 360: 1851-1861.)

Hot flashes are a sudden sensation of warmth, which are usually accompanied by skin reddening, perspiration, palpitation, anxiety, irritability, and even panic, and night sweats. A chill may follow a hot flash because of a subsequent drop in core temperature. Hot flashes vary: they can be several times a week or once per hour, they can be characterized by mild warmth to profuse sweating, and they can last from several seconds to 60 minutes. Such symptoms can disrupt sleep and work and interfere with quality of life.

Almost 60-70% of postmenopausal women have hot flashes, and approximately 10-20% of all postmenopausal women will report intolerable symptoms, including hot flashes. Some women may suffer from these symptoms for up to 15 years (Kronenberg F. "Hot flashes: epidemiology and physiology," Ann N Y Acad Sci, 592:52-86(1990)). Thus, the identification and proper management of menopausal symptoms are crucial to maintaining a woman's quality of life.

Typical hot flashes occur with sudden onsets of sensation of warmth in the chest, which then spreads upward to involve the neck and face. Hot flashes can last from a few seconds to several minutes. However, the severity of the sensations vary greatly both from time to time in the same woman and from woman to woman. Hot flashes may be accompanied by dizziness, nausea, headaches, palpitations, profuse sweating and night sweats. How often a woman experiences hot flashes also varies, ranging from many times a day to once a week or less. Such symptoms can disrupt sleep and work and interfere with quality of life. In some women, hot flashes are provoked by several factors such as hot weather, stress, eating, or drinking alcohol.

Although the pathophysiology of hot flashes is not completely understood, it has been postulated that hot flashes result from a transient lowering of the hypothalamic temperature regulatory set point (Steams et al., "Hot flushes," Lancet, 360:1851-1861 (2002)). Because of the temporal relation between changes in sexual hormone concentrations and the onset of hot flashes, it is believed that such symptoms result from declining estrogen levels or increased gonadotropin concentrations. Thus, hot flashes occur commonly in menopausal women, but also in women taking anti-estrogen drugs, such as tamoxifen. Men on androgen deprivation treatment may also experience such symptoms.

Although estrogen replacement therapy can effectively minimize or prevent hot flashes in women, many women are concerned about potential risks of hormone replacement therapy. This is especially true for women who suffer from breast cancer or have a family history of breast cancer, and/or a history of clotting disorder (Col et al., "Patient-specific decisions about hormone replacement therapy in postmenopausal women," JAMA, 277; 1140-1147 (1997); Gail et al., "The menopause," Lancet, 353:571-580 (1999)).

Various non-hormonal agents have been tested as well, such as clonidine. Clonidine is a centrally-acting $\alpha_2$ adrenergic receptor agonist. It selectively stimulates receptors in the brain that monitor catecholamine levels in the blood. These receptors close a negative feedback loop that begins with descending sympathetic nerves from the brain that control the production of catecholamines (e.g., epinephrine, also known as adrenaline, and norepinephrine) in the adrenal medulla. By tricking the brain into believing that catecholamine levels are higher than they really are, clonidine causes the brain to reduce its signals to the adrenal medulla, leading to lower catecholamine production. The result is a lowered heart rate and blood pressure. In randomized clinical trials, clonidine was shown to be moderately more efficacious than placebo (Goldberg et al., "Transdermal clonidine for ameliorating tamoxifen-induced hot flashes," J Clin Oncol. 12:155-158 (1994); Pandya et al., "Oral clonidine in postmenopausal patients with breast cancer experiencing tamoxifen-induced hot flashes: a University of Rochester Cancer Center Community Clinical Oncology Program study," Ann Intern Med. 132:788-793 (2000)), but adverse effects are common, including dry mouth, dizziness, and blurred vision.

Recent randomized clinical trials also confirmed that some selective serotonin-reuptake inhibitors (SSRI), such as venlafaxine and paroxetine, are more effective than placebo in minimizing the occurrence and severity of hot flashes (Loprinzi et al., "Venlafaxine in management of hot flashes in survivors of breast cancer: a randomised controlled trial," Lancet 356:2059-2063 (2000); Stearns et al., "Paroxetine controlled release in the treatment of menopausal hot flashes: A randomized controlled trial," JAMA 289:2827-2834 (2003)). However, adverse effects with SSRIs are moderate, including headache, agitation, tremor, sedation, and sexual dysfunction.

There are also a number of treatments for hot flashes that appeared to have similar effects in men and women. Decreases of hot flash frequencies in women treated with clonidine are approximately 10-15 percent greater than that seen with placebo. In a double blind, cross over study of clonidine to reduce self-reported hot flash frequency in men, a similar effect was seen, but the difference from placebo effect was not statistically significant. Research has found virtually identical results for men and women receiving megestrol acetate for hot flashes, with approximately an 80 percent reduction in self-reported hot flash frequency compared to a 20 percent reduction with placebo.

Many women seek complementary and alternative medicine (CAM) methods to ease their menopausal symptoms. Compounds used as complementary and alternative medicine can be selected from the group consisting of Soy Vitamin E, Red clover (Trifolium pratense), dong quai, evening primrose oil, black cohosh (*Cimicifuga racemosa*) J Support Oncol 2003; 1:11-21.

Over the last few years, anecdotal reports suggested that antidepressants from the SSRI/SNRI groups might reduce symptoms of hot flashes. These observations led to initial pilot studies and then to randomized placebo controlled clinical trials. In pilot studies, the SNRI venlafaxine (Effexor) and the SSRI paroxetine (Paxil) were associated with hot-flash score reductions on the order of 55%-75%. Other pilot evaluations have suggested that citalopram (Celexa) and mirtazapine (Remeron) also alleviate hot flashes to a similar degree. The first reported randomized clinical trial of one of these newer antidepressants compared three doses of venlafaxine (37.5, 75, and 150 mg/day) to placebo. While low-dose venlafaxine was only mildly more effective than placebo (37% vs 27% reduction in hot-flash scores, respectively), both the moderate and high doses were associated with a statistically significant 61% reduction in hot flash scores. Fluoxetine (Prozac) 20 mg/day was associated with a 50% reduction in hot-flash scores compared to a 36% reduction with placebo (P=0.02).

More recently, anecdotal observations suggesting efficacy led to trials to assess the value of another compound, gabapentin (Neurontin). Gabapentin is a γ-aminobutyric acid (GABA) analog that has been most often prescribed for the treatment of seizures and naturopathic pain. It is also effective in other syndromes, such as panic disorder, social phobia, migraine headache, and essential tremor. Based on anecdotal observations, pilot and randomized trials of gabapentin for the treatment of hot flashes were launched. Results of the pilot trials suggested that gabapentin reduces the incidence of hot flashes by 42%-70%. Benefit was demonstrated regardless of the concurrent use of a stable dose of an SSRI/SNRI agent.

Given the risks of estrogen replacement therapy and marginal benefits of current non-hormonal treatments, there is a continued need for alternative methods or drugs for treating or preventing symptoms associated with menopause, surgery and/or androgen deprivation therapy, including hot flashes.

SUMMARY OF INVENTION

In a first aspect, the invention relates to methods for treating or preventing symptoms of hormonal variation, particularly associated with menopause, surgery and/or androgen deprivation therapy. The method comprises the steps of: identifying a subject having one or more symptoms of hormonal variations, administering an effective amount of a receptor antagonist to the subject, wherein the receptor antagonist binds to at least one selected from the group consisting of a serotonin type 2A ($5\text{-}HT_{2A}$) receptor and a dopamine type 2 ($D_2$) receptor. The receptor antagonist is one selected from risperidone, quetiapine, clozapine, olanzapine, aripiprazole, ziprasidone, zotepine, and 9-hydroxyrisperidone. The preferred receptor antagonists are risperidone and 9-hydroxyrisperidone.

In a second embodiment of the invention, the receptor antagonist is administered with at least one natural compound selected from the the group of complementary and alternative medicine consisting of plant sterols, soy, vitamin E, Red clover, dong quai and black cohosh.

In a third embodiment of the invention, the receptor antagonist is administered with at least one hormonal composition selected from the group consisting of estrogen, premarin, progestin, megestrol acetate and depot medroxyprogesterone.

In a fourth embodiment of the invention, the receptor antagonist is administered with at least one antidopaminergic composition selected from the group consisting of veralipride, methyldopa, bromocriptine and domperidone.

In a fifth embodiment of the invention, the receptor antagonist is administered with at least one antidepressant composition selected from the group consisting of venlafaxine, paroxetine, Fluoxetine, gabapentin and GABA-analog.

In a second aspect, the invention relates to pharmaceutical composition for treating or preventing symptoms of hormonal variation. The pharmaceutical composition comprises an effective amount of a receptor antagonist and a pharmaceutically acceptable carrier, wherein the receptor antagonist binds to at least one receptor selected from the group consisting of a serotonin type 2A ($5\text{-}HT_{2A}$) receptor and a dopamine type 2 ($D_2$) receptor. The receptor antagonist is one selected from risperidone, quetiapine, clozapine, olanzapine, aripiprazole, ziprasidone, zotepine, and 9-hydroxyrisperidone.

In a second embodiment of the invention, the pharmaceutical composition comprises an effective amount of a receptor antagonist, at least one natural compound, and a pharmaceutically acceptable carrier, wherein the receptor antagonist binds to at least one selected from the group consisting of a serotonin type 2A ($5\text{-}HT_{2A}$) receptor and a dopamine type 2 ($D_2$) receptor and the natural compound is selected from the the group consisting of complementary and alternative medicine comprising plant sterols, soy, vitamin E, Red clover, dong quai and black cohosh.

In a third embodiment of the invention, the pharmaceutical composition comprises an effective amount of a receptor antagonist, at least one hormonal composition, and a pharmaceutically acceptable carrier, wherein the receptor antagonist binds to at least one selected from the group consisting of a serotonin type 2A ($5\text{-}HT_{2A}$) receptor and a dopamine type 2 ($D_2$) receptor and the hormonal composition is one selected from the group consisting of estrogen, premarin, progestin, megestrol acetate and depot medroxyprogesterone.

In a fourth embodiment of the invention, the pharmaceutical composition comprises an effective amount of a receptor antagonist, at least one antidopaminergic composition, and a pharmaceutically acceptable carrier, wherein the receptor antagonist binds to at least one selected from the group consisting of a serotonin type 2A ($5\text{-}HT_{2A}$) receptor and a dopamine type 2 ($D_2$) receptor and the antidopaminergic composition is selected from the group consisting of veralipride, methyldopa, bromocriptine and domperidone.

In a fifth embodiment of the invention, the pharmaceutical composition comprises an effective amount of a receptor antagonist, at least one antidepressant composition, and a pharmaceutically acceptable carrier, wherein the receptor antagonist binds to at least one selected from the group consisting of a serotonin type 2A ($5\text{-}HT_{2A}$) receptor and a dopamine type 2 ($D_2$) receptor and the antidepressant composition is selected from the group consisting of venlafaxine, paroxetine, Fluoxetine, gabapentin and GABA-analog.

In a third aspect, the invention relates to pharmaceutical composition for treating or preventing symptoms of hormonal variation. The pharmaceutical composition can be a pharmaceutically acceptable form comprising oral dosage form, injection, inhalation, and transdermal patch. Oral dosage forms, for example, comprise controlled-release dosage form, rapidly dispersed dosage form with a porous network of a matrix composition, and solid rapidly disintegrating dosage form. For example, oral dosage form comprises at least a microparticle composition and a biodegradable and biocompatibly acceptable microparticle polymer carrier. Oral dosage form comprises at least a sustained-release microparticle produced by dissolving in a solvent with a biodegradable and biocompatible polymer to form an organic phase, and extracting the solvent to form microparticles. Oral dosage form comprises a microencapsulated pharmaceutical composition having a selected release profile prepared by a method for preparing microparticles, the method comprising: (a) preparing an emulsion that comprises a first phase and a second phase, wherein the first phase comprises the active agent, a polymer, and a solvent for the polymer; (b) quenching the emulsion in a quench liquid to form microparticles containing the active agent; (c) selecting a degree of intermediate drying of the microparticles to be performed so that the selected release profile is achieved; (d) washing the microparticles; and (e) final drying the microparticles.

Oral dosage form can be a multi-phasic sustained-release microparticle composition, prepared by the process comprising: dissolving in a solvent the active agents and a biodegradable and biocompatible polymer to form an organic phase; extracting the solvent to form microparticles; and combining microparticles having a plurality of sizes to thereby form a composition that delivers the active agent in a multi-phasic manner.

A pharmaceutical composition optionally comprises the active agents, a substance selected from the group consisting of nutrients, vitamins, other active ingredients, sweeteners, flavouring agents, colouring agents, surfactants, preservatives, antioxidants, viscosity enhancers, and minerals.

DETAILED DESCRIPTION OF THE INVENTION

The present invention relates to methods for treating or preventing symptoms associated with hormonal variations, particularly those associated with hormonal changes accompanying menopause, surgery or androgen deprivation therapy. The methods of the invention involve administering an effective amount of therapeutic agents by oral administration, injection, inhalation, transdermal patch, or any other routes commonly used in the art.

Hot flashes are generally systemic and likely result from an alteration in the thermoregulatory set-point centre, which is located in the pre-optic anterior hypothalamus, with involvement of dopamine, serotonin, norepinephrine, and alpha-adrenergic receptors. (Steams et al., "Hot flushes," Lancet 360: 1851-1861 (2002)).

The inventor of the present invention had found that specific subtypes of dopamine, serotonin, and a adrenergic receptors are effective targets for the treatment of hot flashes and other symptoms associated with hormonal variations. Specifically, 5-$HT_{2A}$ antagonist and/or $D_2$ dopamine antagonist are found to be effective in reducing or eliminating symptoms associated with hormonal variations.

Thus, in accordance with some embodiments of the invention, a method for treating or preventing symptoms of hormonal variations may comprise the use of an effective amount of an antagonist of 5-$HT_{2A}$ serotonin receptor and/or $D_2$ dopamine receptor. An effective amount of an antagonist that binds 5-$HT_{2A}$ and/or $D_2$ receptors will depend on the mode of administration, frequency of administration, and the type of pharmaceutical composition used to deliver the compound into a patient, as well as weight, gender, age, and physical conditions of the patient. Generally, effective amounts of such compounds will be about 0.002 mg to about 0.5 mg/kg body weight per day, preferably about 0.005 mg to 0.1 mg/kg body weight per day, and more preferably about 0.005 to about 0.034 mg/kg body weight per day. For example, daily doses may range from about 0.1 to about 25 mg per day for an adult patient weighing about 50 Kg (110 lb), or from about 0.2 to about 50 mg per day for an adult patient weighing about 100 Kg (220 lb). While individual needs vary, determination of optimal range of effective amounts of each compound is within the skills of one skilled in the art. By treating the symptoms of hormonal variations, including hot flashes, embodiments of the invention either reduce the number (occurrence or frequency), duration, and/or severity of symptomatic events. Administering a compound of the invention to a patient may be via any suitable route used for administering similar pharmaceuticals to a patient, including oral administration, injection, and transdermal patch, to name a few. The compound may be administered with any pharmaceutically acceptable carrier or excipient.

Serotonin (5-HT) receptors comprise about 15 different receptors. Type 2 (5-$HT_2$) serotonin receptors are $G_q/G_{11}$ coupled receptors that mediate cellular effects by increasing cellular levels of inositol triphosphate ($IP_3$) and diacylglycerol (DAG). In accordance with some embodiments of the invention, serotonin type 2A receptor is the target for treating or preventing symptoms associated with hormonal variation. Reduction in 5-HT levels increases the sensitivity of 5-$HT_{2A}$ receptor in the hypothalamus, which is involved in thermoregulation. Therefore, modulators of 5-$HT_{2A}$ receptors may be useful in the management of symptoms associated with hormone variations.

In accordance with one embodiment of the invention, risperidone may be used to treat symptoms of hormonal variations. Risperidone BELIVON®, RISPEN®, RISPERDAL® in the United States) is an antipsychotic medication that functions by interfering with the communication among nerves in the brain. Risperidone acts as a 5-$HT_{2A}$ antagonist and can be used to quickly and effectively block the effects of 5-$HT_{2A}$ agonists at a low dose. Risperidone is also a potent dopamine type 2 ($D_2$), and $\alpha_2$ adrenergic receptor antagonist. Thus, risperidone has been used in the treatment of psychotic disorders, for example, schizophrenia. However, as described in the following sections, risperidone has been unexpectedly found to be effective in reducing or eliminating symptoms associated with hormonal variations.

In accordance with another embodiment of the invention, 9-hydroxyrisperidone may be used as a treatment for the symptoms of hormonal variations. 9-Hydroxyrisperidone is the principal active metabolite of risperidone, and they had similar binding profiles and affinity for 5-$HT_{2A}$ receptors and $D_2$ receptors. (Leysen et al., "Risperidone: a novel antipsychotic with balanced serotonin-dopamine antagonism, receptor occupancy profile, and pharmacologic activity," J Clin Psychiatry: 55 Suppl: 5-12 (1994)). Like risperidone, 9-hydroxyrisperidone can effectively treat or prevent the symptoms associated with hormonal variations its antagonist activity for 5-$HT_{2A}$ and/or dopamine receptors.

In addition to risperidone and 9-hydroxyrisperidone, other receptor antagonists that can bind to 5-$HT_{2A}$ and/or $D_2$ dopamine receptors may also be used to control symptoms associated with hormonal variations. These other antagonists, for example, may include quetiapine, clozapine, olanzapine, aripiprazole, ziprasidone, and zotepine.

In accordance with another embodiment of the invention, quetiapine may be used as a treatment for the symptoms of hormonal variations. The antipsychotic effect of quetiapine is thought to be mediated by its antagonist activity against dopamine and 5-HT receptors. Specifically, dopamine receptors $D_1$, $D_2$, and 5-HT receptors, 5-$HT_{1A}$ and 5-$HT_2$ subtypes, are antagonized.

Serial PET scans evaluating the $D_2$ dopamine receptor occupancy of quetiapine have revealed that quetiapine rapidly disassociates from the $D_2$ receptor. Theoretically, this allows for normal physiological surges of dopamine to elicit their normal effects in areas such as the nigrostriatal and tuberoinfundibular pathways, thus minimizing the risk of side effects such as pseudo-Parkinsonism and elevations in prolactin. Quetiapine also has an antagonistic effect on the $H_1$ histamine receptor. This may be responsible for the sedative effect of the drug.

In accordance with some embodiments of the invention, clozapine may be used as a treatment for the symptoms of hormonal variations. Clozapine is classified as an 'atypical' antipsychotic drug because its profile of binding to dopamine receptors and its effects on various dopamine-mediated behaviors differ from those exhibited by more typical antipsychotics. In particular, clozapine has a high affinity for the D4 receptor and it also interferes to a lower extent with the binding of dopamine with $D_1$, $D_2$, $D_3$ and $D_5$ dopamine receptors. However, clozapine does not induce catalepsy, nor does it inhibit apomorphine-induced phenotype in animal models seen with 'conventional' neuroleptics. This evidence suggests that clozapine is preferentially more active at limbic than at striatal dopamine receptors and may explain its relatively mild extra-pyramidal side effects and its strong anti-cholinergic activity. Clozapine is also a strong antagonist of different subtypes of adrenergic, cholinergic, histaminergic and serotonergic receptors.

In accordance with some embodiments of the invention, olanzapine may be used as a treatment for symptoms of hormonal variations. Olanzapine is structurally similar to clozapine, and has a high affinity for dopamine and serotonin receptors. Olanzapine has a low affinity for histamine, cholinergic muscarinic and α-adrenergic receptors. The mechanism of action of olanzapine is unknown. However, it is thought that olanzapine's antipsychotic activity is mediated primarily by antagonism of dopamine receptors, specifically $D_2$ dopamine receptor. 5-HT antagonism may also play a role in the effectiveness of olanzapine. However, the significance of $5-HT_{2A}$ antagonism is debated among researchers.

In accordance with some embodiments of the invention, aripiprazole may be used as a treatment of symptoms of hormonal variations. Aripiprazole (Abilify® from Bristol-Myers Squibb) is a new atypical antipsychotic medication awaiting approval by the FDA for the treatment of schizophrenia. Aripiprazole has been approved by the FDA for the treatment of acute manic and mixed episodes associated with bipolar disorder. Aripiprazole appears to mediate its antipsychotic effects primarily by acting as a partial agonist of the $D_2$ receptor. Partial agonism at $D_2$ receptors has been shown to modulate dopaminergic activity in areas where dopamine activity may be high or low, such as the mesolimbic and mesocortical areas of the schizophrenic brain, respectively. In addition to partial agonist activity of the $D_2$ receptor, aripiprazole is also a partial agonist of the $5-HT_{1A}$ receptor. Like other atypical anti-psychotics, aripiprazole exhibits antagonist activities against the $5-HT_{2A}$ receptor. Aripiprazole has moderate affinities for histamine and α-adrenergic receptors, but no appreciable affinity for cholinergic muscarinic receptors.

In accordance with some embodiments of the invention, ziprasidone may be used as a treatment of symptoms of hormonal variations. Ziprasidone has a high affinity for dopamine, serotonin, and alpha-adrenergic receptors and a moderate affinity for histaminic receptors. Ziprasidone is somewhat unique among the "atypicals" in that it can also inhibit synaptic reuptake of serotonin and norepinephrine, although the clinical significance of this is unknown. The mechanism of action of ziprasidone is unknown. However, it is thought that its antipsychotic activity is mediated primarily by its antagonism against dopamine receptors, specifically $D_2$ dopamine receptor. Serotonin antagonism may also play a role in the effectiveness of ziprasidone, but the significance of $5-HT_{2A}$ antagonism of ziprasidone is debated among researchers. Antagonism at histaminic and alpha adrenergic receptors likely explains some of the side effects of ziprasidone, such as sedation and orthostasis.

In accordance with some embodiments of the invention, zotepine may be used as a treatment of symptoms of hormonal variations. Zotepine has a high affinity for the $D_1$ and $D_2$ dopamine receptors. It also affects the $5HT2_A$, $5HT2_C$, $5HT_6$, and $5HT_7$ receptors. In addition, it can also inhibit the reuptake of noradrenaline.

Pharmaceutical Formulation

The pharmaceutical formulation of present invention can be prepared by examples described in previous patents and published documents as follows.

U.S. Pat. No. 5,648,093 provides methods for preparing different solid dosage forms; which are incorporated herein by reference.

It is an object of the present invention to provide an improved solid dosage form of the type comprising a porous network of matrix material that disperses rapidly in water in less than about ten seconds. The matrix material is made up from at least about 0.1% by weight of a matrix forming agent selected from the group consisting of gelatin, pectin, soy fiber protein and mixtures thereof, and one or more amino acids having from about 2 to 12 carbon atoms. The preferred amino acid is glycine, while the preferred matrix forming agent is gelatin and/or pectin. In a particularly preferred embodiment, the dosage form additionally comprises mannitol.

The dosage form is formed by subjecting a matrix material solution to lyophilization or solid-state dissolution. In a preferred embodiment of the present invention, the matrix material solution used to form the inventive dosage form contains from about 0.1% to about 15% matrix material by weight. Preferably, the matrix material solution comprises from about 0.1% to about 3% of the matrix forming agent by weight, from about 0.5% to about 10% of the one or more amino acids by weight, and from about 0.5% to about 10% mannitol by weight.

Where lyophilization is used to form the inventive solid dosage form, any active or bioactive agent contained in the dosage form may be advantageously present in a coated form. In this embodiment, the active or bioactive agent is present in particulate form and the particles of the agent are coated with an appropriate coating agent(s) to protect the active or bioactive agent from process solvents, the aqueous environment of the oral or other mucosal cavity, or environmental conditions that would dissolve or deteriorate said active. These coating materials may be selected from natural or synthetic polymers that are either hydrophilic or hydrophobic in nature or other hydrophobic materials such as fatty acids, glycerides, triglycerides and mixtures thereof. In this way, the taste of the active or bioactive agent may be masked, while at the same time permitting the solid dosage form to dissolve rapidly upon contact with physiological solvents. Examples of active agents that may be coated in accordance with the present invention include acetaminophen, ibuprofen, chlorpheniramine maleate, pseudoephedrine and dextromethorphan.

The dosage forms of the present invention are quite robust in comparison to prior art dosage forms, especially those prepared by lyophilization. Also, the inventive dosage forms exhibit greatly reduced or no shrinkage under high temperature or humidity conditions when compared to prior art dosage forms, especially those prepared using lyophilization.

It is also an object of the present invention to provide an inexpensive method of removing solid solvent from a solidified mixture that prevents or reduces the incidence of cracking of the final preparation.

It is an additional object of the present invention to provide a method of removing solid solvent from a solidified mixture wherein the incidence of meltback during the process is reduced or eliminated.

It is a further object of the present invention to provide a method of removing solid solvent from solidified pharmaceutical mixtures so that the prepared dosage forms exhibit rapid dissolution in appropriate solvents.

It is another object of the present invention to provide a method of preparing a dosage form having uniform porosity.

It is a further additional object of the present invention to provide dosage forms that include active ingredients, such as pharmaceuticals, nutrients, diagnostics, confectioneries, fertilizers and insecticides.

It is yet another object of the present invention to provide a method of preparing a dosage form having adequate strength for handling.

It is a specific object of the present invention to provide a solid-state dissolution method of removing solid solvent from solidified samples. According to the inventive method, one or more delivery matrix forming agents (and optionally a sample to be delivered) are dissolved or dispersed in a first solvent, solidified and subsequently contacted with a second solvent at a temperature at or higher than the solidification point of the second solvent and at a temperature at or lower than the solidification point of the first solvent. The first solvent in the solidified state is substantially miscible with the second solvent, while the matrix forming agent(s) (and sample if present) are substantially insoluble in the second solvent. The first solvent is thereby substantially removed from the solidified matrix yielding a solid matrix (optionally containing the sample) substantially free of the first solvent.

It is an additional specific object of the present invention to provide a solid-state dissolution method for preparing unit dosage forms wherein a first solvent is removed from the dosage form while it is still in the solid state. According to this inventive method, one or more matrix forming agents (and optionally a sample to be delivered) are dispersed or dissolved in a first solvent and a unit volume of the solution or dispersion is then solidified. The solidified unit volume of sample is next contacted with a second solvent, which is substantially miscible with the first solvent in the solidified state. The second solvent is at a temperature at or higher than the solidification point of the second solvent and at a temperature at or lower than the solidification point of the first solvent, the matrix forming agent (and sample if present) being substantially insoluble in the second solvent. Thus, the first solvent is substantially removed from the solidified unit volume yielding a dosage form unit (containing a unit dosage amount of the sample if present) that is substantially free of the first solvent. In one alternative, the processed dosage form may be contacted with a bioactive agent to yield a dosage form having a specific amount of the bioactive agent dispersed therethrough.

It is a further object of the present invention to provide a solid carrier system for chemicals that a user may add to a medium to instantaneously obtain a solution or dispersion of desired concentration.

The method of the present invention produces dried samples with minimal cracking or meltback of the processed sample.

The resulting preparations exhibit uniform high porosity while having sufficient strength, i.e., resistance to disintegration or crumbling under normal manufacturing and handling conditions.

It is another object of the present invention to provide improved dosage forms containing amino acids having from 2 to 12 carbon atoms as matrix forming agents. In a particularly preferred embodiment, glycine forms a primary part of the matrix of the porous dosage form. This aspect of the present invention provides improved dosage forms having the following advantages: quick dissolution and disintegration, pleasant taste and mouthfeel, nutritional value, low calorie content and noncariogenicity.

In the realm of pharmaceutical use, pharmaceutical dosage forms prepared according to the present invention exhibit rapid dissolution upon contact with physiological solvents, such as water, saliva, or gastrointestinal fluids. Therefore, the present inventive pharmaceutical dosage forms provide a more rapid dispersion of the pharmaceutical within the body upon ingestion.

U.S. Pat. No. 5,770,231 provides methods for preparing different pharmaceutical formulations comprising a sustained-release microparticle produced by dissolving in a solvent an active agent and a biodegradable and biocompatible polymer to form an organic phase. Examples 1-4 of the '231 Patent are incorporated herein by reference.

The following examples are to illustrate embodiments of the invention. These examples are for illustrative purpose only. One of ordinary skill in the art would appreciate that these examples are not exhaustive and they are not intended to limit the scope of the invention. In addition, it should be understood that throughout this specification.

EXAMPLES

The following examples are provided to illustrate that embodiments of the present invention can reduce the symptoms of hormone variations, including hot flashes, night sweats, and blood pressure fluctuations. Embodiments of the invention are effective for patients under various conditions. However, one of ordinary skill in the art would appreciate that these examples are for illustration only and by no means are intended to limit the scope of the invention.

Embodiments of the invention involve administering a therapeutically effective amount of an antagonist (such as risperidone or 9-hydroxyrisperidone) of $5\text{-HT}_{2A}$ and/or $D_2$ dopamine receptor to alleviate symptoms associated with hormone variations. For example, risperidone has been used on several patients to successfully alleviate the occurrence of hot flashes or other symptoms of hormonal variations. The following describe four specific examples from four different patients to illustrate the effectiveness of risperidone in alleviating symptoms associated with hormone variations. One of ordinary skill in the art would appreciate that these specific examples are not intended to limited the scope of the invention. For example, embodiments of the invention may use other regimens, including other antagonists of $5\text{-HT}_{2A}$ and/or $D_2$ dopamine receptors.

Example 1

Risperidone Resolved Hot Flashes in a Case with Hysterectomy

A 68-year-old woman was admitted to the hospital in December of 2004 due to hot flashes, hypertension, and restlessness. She had been told that she was suffering from essential hypertension for 16 years and had taken anti-hypertension medications for several years. However, her blood pressure still fluctuated and frequently dropped below critical level after taking sublingual adalate (10 mg) for sudden onsets of high blood pressure. She had no history of psychiatric or systemic diseases, except for a total abdominal hysterectomy at age 45. On admission, it was observed that her hot flash attacks occurred many times a day, lasting a few minutes and was usually followed by high blood pressure up to 180-200/84-96 mmHg, general shivers, and anxiety for 20-60 minutes. Such clinical symptoms started around age 50 and grew progressively worse.

Her biochemical and hematological results, such as sodium and potassium levels, 140 mmol/L and 4.0 mmol/L, respectively, were all within normal ranges. Plasma cortisol levels were within the normal range and showed diurnal rhythm. The plasma adrenaline, nor-adrenaline, VMA, epinephrine, and dopamine levels as well as thyroid hormones, including T3, T4, and TSH, were also normal. SSR and RRIV tests to assess sympathetic and parasympathetic functions, respectively, demonstrated her autonomic nervous system was normal. EEG showed no focal epileptiform discharges nor abnormal background activities. Brain MRI showed aging brain changes, but no lesion in hypothalamus or brain stem. 24-hour Holter's scan showed normal sinus rhythm. Echocardiography demonstrated normal cardiac chamber size, normal LV systolic performance, and wall motion.

After one month of observation, the patient received treatments of PREMARIN® 0.625 mg/day, PROZAC® 20 mg/day and TOFRANIL® 20 mg/day, each for 1-2 months with limited success. Because estrogen withdrawal may alter the thermoregulatory set-point located in the hypothalamus, by increasing the sensitivity of hypothalamic 5-HT2A receptor, a regimen of a $5\text{-HT}_{2A}$ antagonist may provide an effective therapy for symptoms of hormonal variations, such as hot flashes. Thus, the patient was treated with risperidone (2 mg/day). After three days of treatment, her hot flashes reduced markedly to a frequency of once per 1-2 weeks. Associated symptoms, such as palpitation and anxiety, also improved significantly. Thereafter, the dosage of anti-hypertension drugs was reduced. With the patient's permission, risperidone therapy was discontinued and hot flashes reoccurred within 2-3 days after discontinuing the treatment. The symptoms were again alleviated 3-4 days after resuming risperidone treatment.

Example 2

Risperidone Resolved Hot Flashes of Natural Menopause

Patient 2 was a 57-year-old woman who began developing intolerable hot flashes and night sweats after natural menopause that occurred seven years ago. Although she responded well to hormone replacement therapy (PREMARIN® 0.625 mg per day), she discontinued the therapy one year prior to this study because she was concerned about the potential risk of breast cancer. One month after discontinuing hormone replacement therapy, she developed hot flashes up to ten times per day, night sweats up to three times per night that disrupted her sleep, and headaches. The patient then sought neurological consultation. The patient also suffered from headaches twice per day and fluctuating blood pressure. Risperidone was started at a dose of 2 mg per day and the patient reported that the occurrence of hot flashes reduced markedly two days after starting risperidone treatment and was completely eliminated by day 7. In addition, she slept well and her blood pressure stabilized. To assess the relationship between risperidone therapy and the resolution of hot flashes, risperidone was tapered off over 2 days. The patient experienced hot flashes and night sweats again two days after risperidone treatment was completely discontinued. Risperidone 2 mg daily was resumed and the patient has not suffered another hot flash since.

Example 3

Risperidone Resolved Hot Flashes in a Perimenopausal Case

Patient 3 was a 46-year-old woman who was diagnosed with perimenopause, based on increased levels of follicle-stimulating hormone, increased variability in menstrual cycle length, development of hot flashes, and insomnia. The patient had had these symptoms for two years. She responded well to estrogen therapy. Because of health risks, the patient discontinued estrogen treatment and sought supplementary therapy, such as soy isoflavones, but without success. Risperidone treatment (1 mg per night) was started. At that time, the patient was experiencing seven hot flashes per day. The patient reported that the frequency and intensity of her hot flashes were markedly reduced three days after starting risperidone therapy. With her permission, risperidone was tapered off over two days, and the hot flashes developed again three days later. After risperidone treatment (1 mg daily) was resumed, the patient no longer experienced hot flashes, and the quality of her sleep and her life improved. Three months later, the dosage of risperidone was decreased to 0.25 mg or less per day, and the patient's hot flashes were still markedly eliminated.

Example 4

Risperidone Resolved Residual Hot Flashes in a Case with Hormone Replacement Therapy Patient 4 was a 56-year-old woman who had developed hot flashes, with a frequency of once per hour, palpitation, insomnia, headache, restlessness, and unstable blood pressure for over seven years. Initially, the patient visited a psychiatrist for her sleep disorder and a cardiovascular specialist for her high blood pressure. A year later, because of intolerable hot flashes and other menopausal symptoms, she received hormone replacement therapy (DIVINA®). Although her hot flashes were reduced to twice per day, headaches persisted and her blood pressure fluctuated from 180 to 210/110 to 90 mm Hg despite treatment with anti-hypertension drugs. The patient was started on risperidone treatment, 1 mg at bedtime for the first two days, followed by 2 mg per night, for residual hot flashes. The patient's hot flashes were completely eliminated three days after starting the risperidone therapy. Additionally, the patient was able to take hormone four times a day and discontinue the use of all anti-hypertension drugs because her blood pressure stabilized within the normal range.

The above data clearly show that risperidone or similar receptor antagonists are effective in alleviating the symptoms associated with hormonal variations, such as hot flashes and blood pressure fluctuations. It is also contemplated that administration of a compound of the invention for alleviating symptoms associated with hormonal variations may be carried out in combination with other suitable therapeutic treatments which are useful for treating symptoms of hormonal variations, including hot flashes.

What is claimed is:

1. A method for treating one or more symptoms of hormonal variation associated with orchiectomy surgery or androgen deprivation therapy in a subject, comprising the steps of:
    identifying a subject having one or more symptoms of hormonal variation associated with orchiectomy surgery or androgen deprivation therapy, and
    administering an effective amount of risperidone and/or 9-hydroxyrisperidone to the subject, wherein the symptoms are selected from the group consisting of hot flashes, dizziness, nausea, palpitations, profuse sweating, and night sweats.

2. The method of claim 1, further comprises administering a second active ingredient selected from the group consisting of a natural compound for complementary and alternative medicine, a hormonal composition, an antidopaminergic composition, and an antidepressant composition.

3. The method of claim 2, wherein the natural compound for complementary and alternative medicine is plant sterols, soy, vitamin E, Red clover, dong quai, or black cohosh.

4. The method of claim 2, wherein the hormonal composition comprises estrogen, premarin, progestin, megestrol acetatem or depot medroxyprogesterone.

5. The method of claim 2, wherein the antidopaminergic composition comprises veralipride, methyldopa, bromocriptine, or domperidone.

6. The method of claim 2, wherein the antidepressant composition comprises venlafaxine, paroxetine, fluoxetine, gabapentin, or GABA-analog.

7. The method of claim 1, wherein the risperidone or 9-hydroxyrisperidone is provided in a pharmaceutically acceptable form of oral dosage form, injection, inhalation, or transdermal patch.

8. The method of claim 1, wherein the symptoms are hot flashes and night sweats.

9. The method of claim 1, wherein the symptoms are hot flashes.

10. The method of claim 1, wherein the administering is oral administration.

11. The method of claim 1, wherein an effective amount of risperidone is administered.

12. The method of claim 1, wherein the symptoms are associated with androgen deprivation therapy.

13. The method of claim 9, wherein the effective amount is 0.005-0.1 mg/kg body weight per day.

14. The method of claim 9, wherein the effective amount is 0.005-0.034 mg/kg body weight per day.

* * * * *